United States Patent [19]
Rice et al.

[11] Patent Number: 5,832,006
[45] Date of Patent: Nov. 3, 1998

[54] PHASED ARRAY RAMAN LASER AMPLIFIER AND OPERATING METHOD THEREFOR

[75] Inventors: Robert R. Rice, Chesterfield; Mark S. Zediker, Florissant, both of Mo.

[73] Assignee: McDonnell Douglas Corporation, St. Louis, Mo.

[21] Appl. No.: 800,296

[22] Filed: Feb. 13, 1997

[51] Int. Cl.[6] ................................................ H01S 3/30
[52] U.S. Cl. .................................. 372/3; 372/3; 372/22; 372/6; 372/9
[58] Field of Search ................................ 372/3, 22, 6, 9; 359/327

[56] References Cited

U.S. PATENT DOCUMENTS

| | | | |
|---|---|---|---|
| 5,058,117 | 10/1991 | Shoshan et al. | 372/3 |
| 5,260,954 | 11/1993 | Dane et al. | 372/3 |
| 5,265,106 | 11/1993 | Garcia | 372/3 |
| 5,453,814 | 9/1995 | Aiyer | 359/327 |

*Primary Examiner*—Leon Scott, Jr.
*Attorney, Agent, or Firm*—Raymond Powell; Robert Westerlund; R A Westerlund

[57] ABSTRACT

A phased array Raman laser amplifier includes a beam generator for generating a fundamental laser beam and a Raman seed frequency laser beam, and a fiber optic laser amplifier array for forming a diffraction limited output laser beam at the Raman seed frequency by amplifying the fundamental laser beam to a power level corresponding to the Stimulated Raman Scattering (SRS) threshold to thereby pump the SRS process and provide Raman gain to the Raman seed frequency laser beam. The fiber optic laser amplifier includes a beam splitter receiving the fundamental laser beam and the Raman seed frequency laser beam and generating N secondary fundamental and N Raman seed frequency laser beams, N parallel rare earth doped optical fiber sections, each of the optical fiber sections amplifying a respective one of the N secondary fundamental laser beams to thereby produce N tertiary laser beams at the power level corresponding to the Stimulated Raman Scattering (SRS) threshold to thereby pump the SRS process and provide Raman gain to the N Raman seed frequency laser beams to thereby produce N amplified Raman seed frequency laser beams, and an optical combiner for receiving at least the N Raman seed frequency laser beams and for generating the diffraction limited output laser beam at the Raman seed frequency. Preferably, N is an integer greater than or equal to 2. A method for operating the phased array Raman laser amplifier is also described.

16 Claims, 9 Drawing Sheets

PHASED ARRAY RAMAN LASER AMPLIFIER AND OPERATING METHOD THEREFOR

BACKGROUND OF THE INVENTION

The present invention relates generally to Raman laser amplifiers. More specifically, the present invention relates to phased array Raman laser amplifiers. A method of operating the phased array Raman laser amplifier is also disclosed.

There are many applications that require high average laser power at very precise wavelengths, which wavelengths do not correspond to efficient laser transitions. Two important exemplary applications are the use of a laser to excite the sodium layer in the upper atmosphere to produce a "guide star" for adaptive optical compensation of atmospherics, and the use of precisely tuned laser sources to photo dissociate chemical compounds of specific isotopes and thereby allow separation of isotopic species (e.g., $U^{235}$ from $U^{238}$).

The "guide star" application, which has both military and scientific importance, requires the production of several hundred watts of near-diffraction-limited power at 589.5 nanometers (nm), i.e., the sodium resonance wavelength. The back-scattered resonance fluorescence from the sodium layer in the upper atmosphere can serve as an effective point source to correct for the effects of the atmosphere, much as can be done with the light from a bright natural star. It will be appreciated that there are two reasons to perform such atmospheric compensation:

1) to improve image quality for satellite and astronomical observations; and 2) to allow high energy laser power to be efficiently focused on space targets, as in the Ground Based Laser Anti-Satellite (ASAT) program.

One conventional approach for producing a high power laser beam at 589 nm could be considered the pulsed dye laser technology initially developed by Lawrence Livermore National Laboratory (LLNL) and selected by the U.S. Air Force (USAF) for the artificial "guidestar" source. The reason the LLNL dye laser, which is a modified pump laser first used in the isotope separation program mentioned above, has turned out to be unacceptable is that the emitted waveform, i.e., 100 ns pulses at a 30 kHz rate, does not efficiently excite the sodium vapor at high altitude. The radiated power required would be more than 500 watts; extending the power capabilities of a pulsed dye laser system to the required output power level is not considered feasible from either a cost or a technological perspective. Calculations by the USAF indicate that a 589 nm laser producing 350 ns pulses at a 100 MHz rate would be far more effective. The actual waveform desired is a 160 ms pulse burst of the short pulses described above at a 1 kHz burst rate. The USAF also funded development of a Raman shifted solid state laser oscillator running at 1178 nm. It will be appreciated that the output laser beam could be frequency doubled to 589 nm. To date, the power level achieved by the Raman shifted solid state laser oscillator has been far too low for use in the "guidestar" application.

Figure 1:
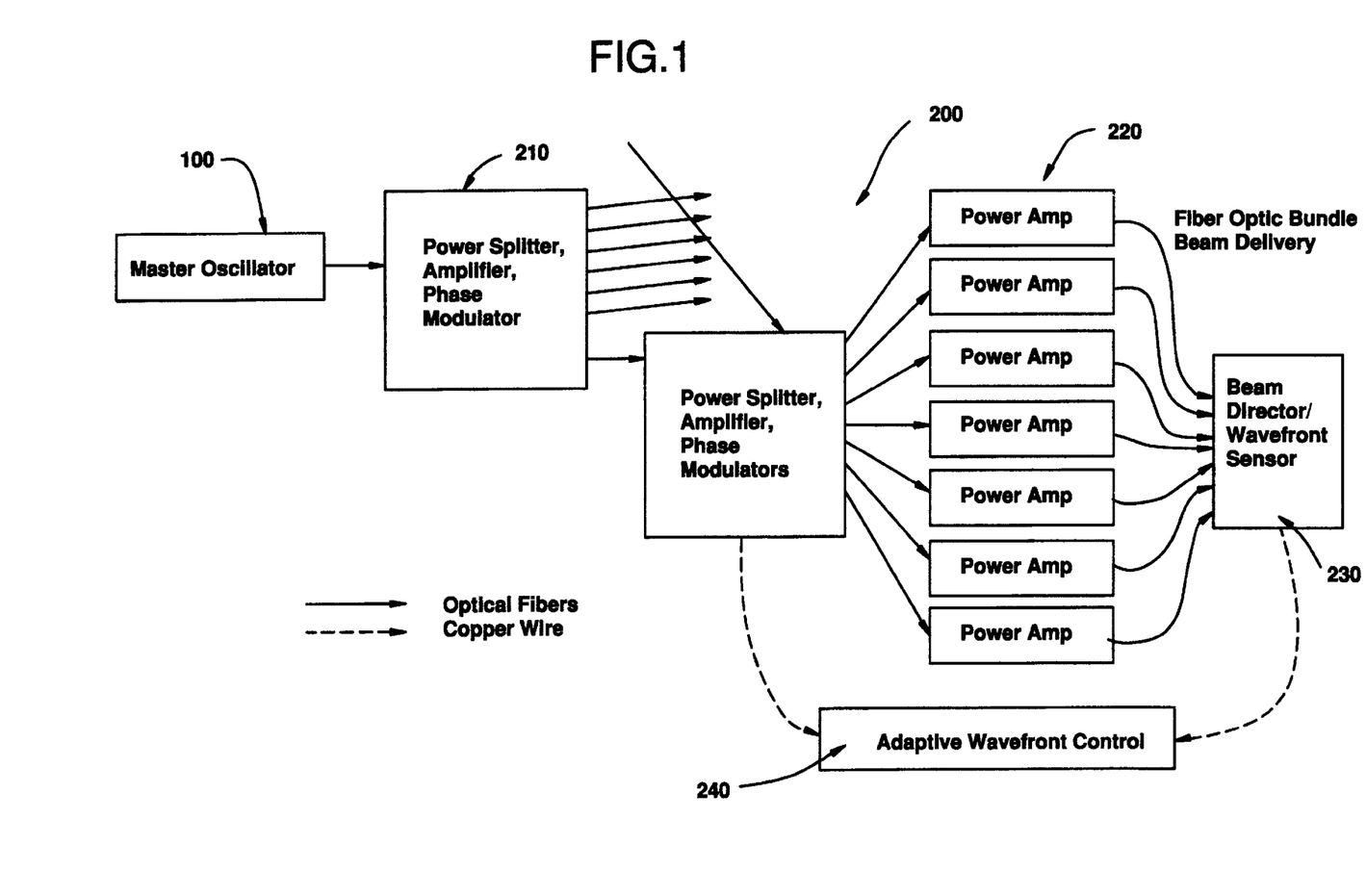
FIG. 1 is a high level block diagram of selected components of a previously proposed fiber optic amplifier.

One proposed laser transmitter which has the requisite power output characteristic is a Master Oscillator—Phased Power Amplifier Array (MO)-(PPAA) laser system previously disclosed in commonly-assigned, co-pending U.S. application Ser. No. 08/782,175, which was filed on Jan. 14, 1997, and which application is incorporated herein by reference for all purposes. As illustrated in FIG. 1, the MO-PPAA laser system includes a MO 100 coupled to a fiber optic power amplifier 200. MO 100 is a stable, very narrow linewidth, laser, which is operating in a $TEM_{00}$ mode at a frequency within the gain spectrum of the power amplifier 200 and which can be coupled by optical fiber to deliver a continuous wave signal to downstream components (not shown).

It will be appreciated that the master oscillator laser 100 can be any conventional master oscillator laser, although the master oscillator is likely a fiber laser oscillator. Some additional conventional components are understood to be part of any practical MO-PPAA laser system and have been omitted. For example, one of ordinary skill in this particular art would appreciate that an optical isolator would be located immediately downstream of the master oscillator 100 to prevent feedback from downstream components, e.g., power amplifier 200, that would induce instability in the master oscillator 100. The details of such components are well known to those skilled in the art and will not be discussed further.

Although a single fiber power amplifier 200 will suffice for some short range applications, a coherent array of optical fiber amplifiers collectively forming the fiber optic power amplifier 200 can be particularly advantageous for those specific applications requiring high output power. One such arrangement of a coherent phased array of fiber optic amplifiers generating high power laser beam is shown in FIG. 1, for example, as needed in long range laser system applications. This particular laser power amplifier is also described in detail in copending, commonly assigned U.S. patent application Ser. Nos. 08/471,870 and 08/611,474, which applications are also incorporated herein by reference for all purposes.

Figure 2A:
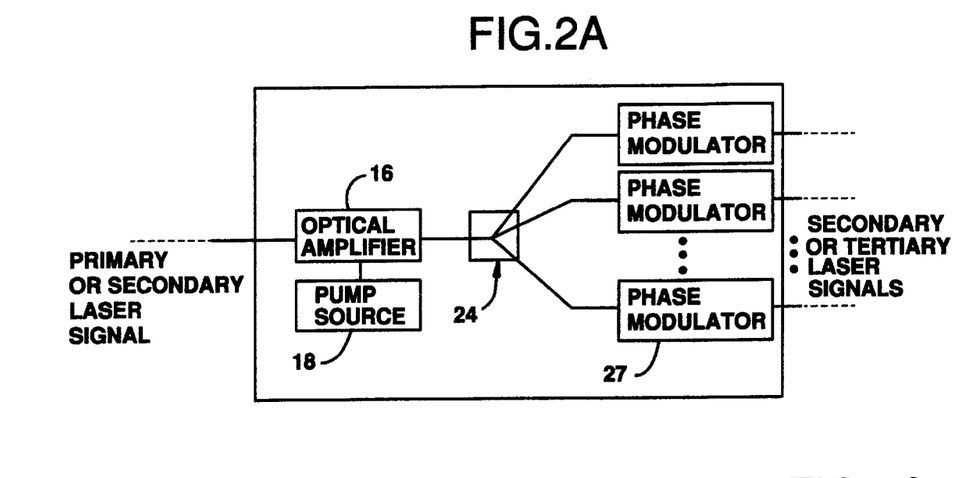
FIGS. 2a through 2c illustrate alternative preferred configurations of the selected optical elements within the fiber optic power amplifier as illustrated in FIG. 1.

It will be appreciated that the power splitter, amplifier and phase modulator elements 210 in FIG. 1 may be arranged in various configurations other than the exemplary arrangement illustrated in that Figure. The illustrated fiber optic power amplifier 200 of FIG. 1 includes a first stage composed of a first beam splitter element 210, for splitting a received laser beam into a number N of secondary laser beams. Each of the secondary laser beams is provided to a second beam splitter element 210, which produces a number M of tertiary laser beams from a respective one of the secondary laser beams. Each of the tertiary laser beams is amplified by a respective fiber power amplifier generally denoted 220. It should be mentioned that although two separate stages of beam splitter elements 210 and one amplifier stage 220 are depicted in FIG. 1, the fiber optic power amplifier 200 can have more or less amplification stages. For example, when the first and second beam splitter elements 210 include an optical amplifier 16 pumped by a pump source 18, a beam splitter 24 and, optionally, a number N×M of phase modulators, respectively, a total of three amplification devices are included in the power amplifier 220. See FIG. 2a.

Figure 2B:
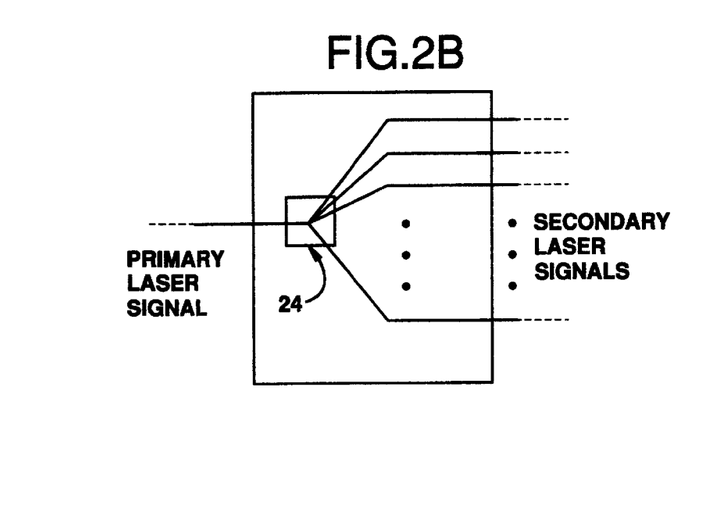
Figure 2C:
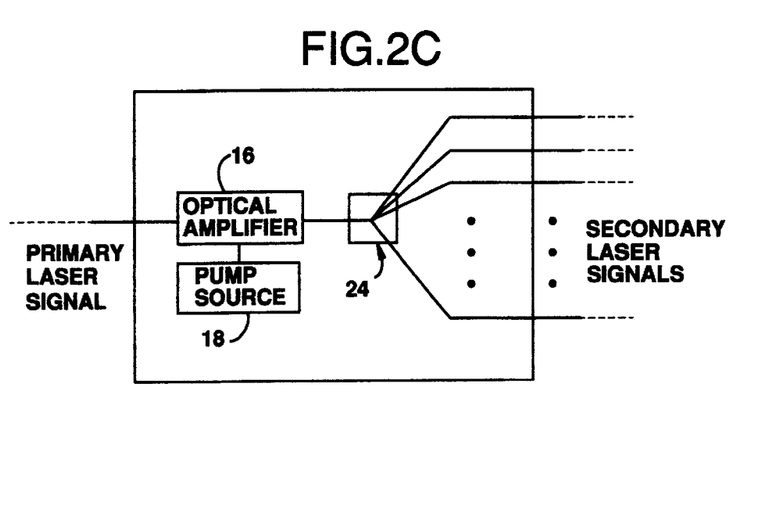

Moreover, alternative configurations are possible. For example, the number of series connected elements 210 can be any number greater than or equal to 2. Moreover, element 210 is not limited to the arrangement illustrated in FIG. 2a. For example, the first stage element 210 need not include either an amplifier 16 or a phase modulator 27 (FIG. 2b); alternatively, the first stage element 210 may include optical amplifier 16 but omit phase modulator 27. Needless to say, additional amplifier stages can also be provided.

It will be noted that the fiber optic power amplifier 200 includes a phase modulator 27 in each optical path. These phase modulators 27 are provided to ensure that all of the N×M laser beams output by power amplifier 200 arrive at the output of the power amplifier 200 with a predetermined phase profile to minimize transmission losses. The power amplifier 200 thus includes a waveform sensor 230 in the output optical path. The waveform sensor 230 produces sensor signals which are provided to phase modulators 27 in element 210 via an adaptive waveform controller 240. Examples of the construction and operation of waveform sensor 230 and waveform controller 240 are provided in above-referenced copending, commonly assigned U.S. patent application Ser. Nos. 08/471,870 and 08/611,474.

Thus, in the system depicted in FIG. 1, the master oscillator 100 generates a signal at a low power level that is coupled into an optical fiber. The signal, which must be within the gain band of the rare earth dopant used in the system, is amplified and split among many fiber optic power amplifiers in power amplifier 200. Each stage of the power amplifier 200 amplifies the signal to a high level and delivers it to a summing aperture with appropriate beam forming optics (not shown). The phase of the signal from each beam line is individually controlled to form a diffraction limited beam from the array. The master oscillator 100 defines the wavelength and waveform of the signal amplified and radiated by the MO-PPAA laser system, subject to the wavelength constraints mentioned previously.

Nonlinear optical processes such as Stimulated Brillouin Scattering (SBS) and Stimulated Raman Scattering (SRS) can rob power from a coherently amplified lightwave produced in power amplifier 200. SBS is a narrowband process whereby forward-going light is scattered into a backward-going wave shifted by 11 Ghz, more or less. SRS, however, is a broad band effect whereby energy from the original wave is downshifted by 53 nm, nominally, into another forward-going wave. Both of these processes have a threshold-like behavior whereby, for a given fiber length, above a certain power level, significant energy is extracted from the coherently amplified wave into the scattered wave at a different wavelength. Below this threshold, the nonlinear process is not a problem.

Figure 3:
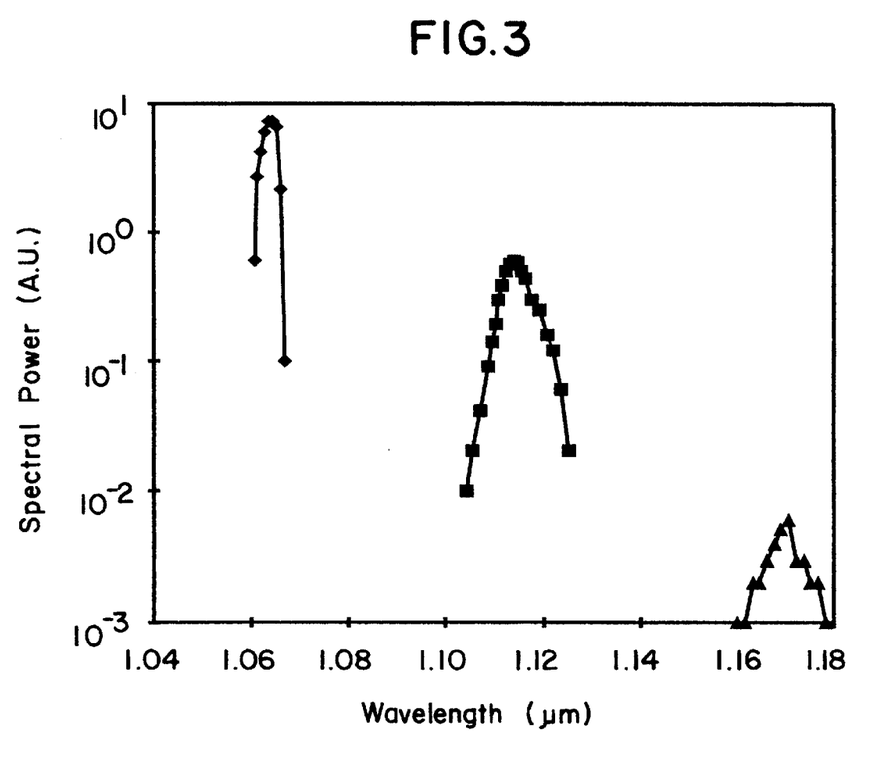
FIG. 3 is a series of curves depicting spatial power distribution with respect to wave length in an optical fiber operating above the Stimulated Raman Scattering (SRS) threshold.

Spectral data of light emitted from an exemplary fiber 40 meters in length is shown in FIG. 3. The maximum coupled Nd:YAG power sent down the fiber was 130 Watts at the peak, which is slightly above the Raman threshold. The spectral line of the unshifted 1.064 $\mu$m light is narrowest. The first-order Raman line is downshifted by 53 nm to 1.117 $\mu$m, as expected from silica-glass fibers. The Raman light can itself be Raman shifted another 53 nm into a second-order Raman line, which is clearly shown in FIG. 3. It will be appreciated that a weak emission at 1178 nm is also illustrated in FIG. 3.

Figure 4:
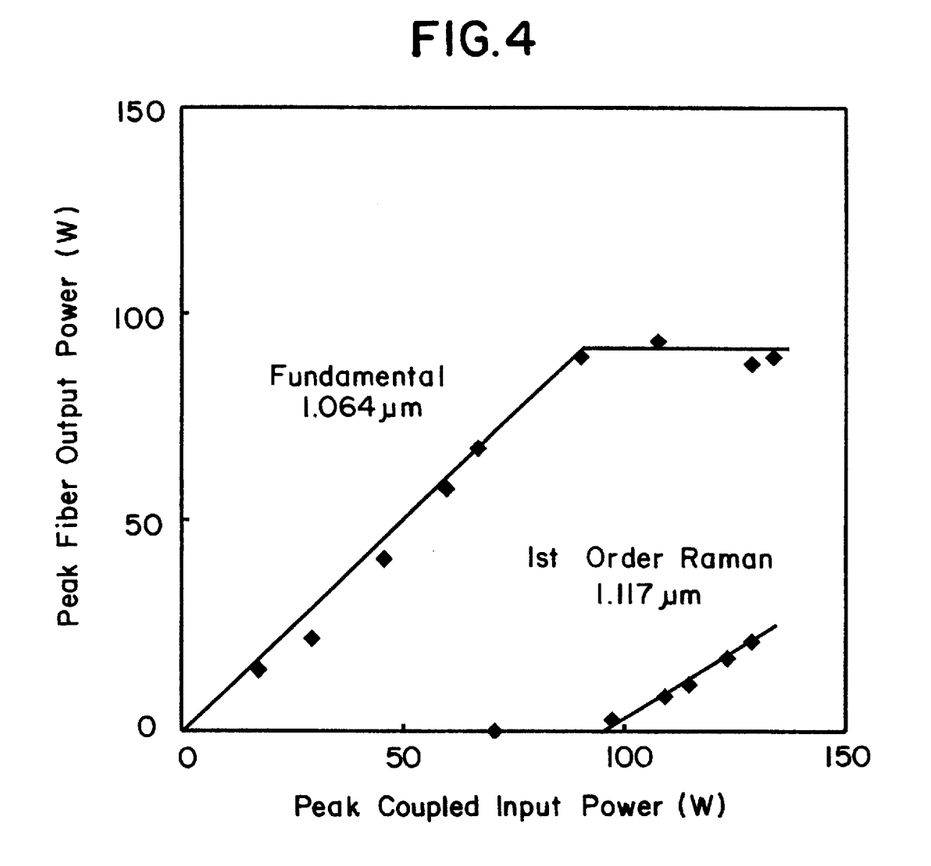
FIG. 4 presents a series of curves illustrating the effects of coupling a laser beam having an input power above the SRS threshold into an optical fiber.

FIG. 4 illustrates how much light is emitted from this same exemplary fiber at the fundamental and Raman wavelengths as a function of light power coupled into the fiber. The data demonstrate that SRS is a highly nonlinear process. Once the SRS threshold is reached, the fundamental light power is virtually clamped and the excess power is shifted to the Raman wavelength. It will be appreciated that the Raman light is self aperturing; it can only be generated in, not outside, the core.

The SRS threshold for the exemplary 40 meter piece of optical fiber discussed above is approximately 100 Watts. It should be pointed out that the SRS process is highly non-linear and thus very sensitive to small variations in parameters such as the mode size, fiber length and core dopants. Since the SRS is highly dependent on these parameters, it is feasible to increase the SRS threshold by increasing the mode diameter, and vice versa. Simulations show that small changes can result in significant increases or decreases in the SRS gain.

Figure 6:
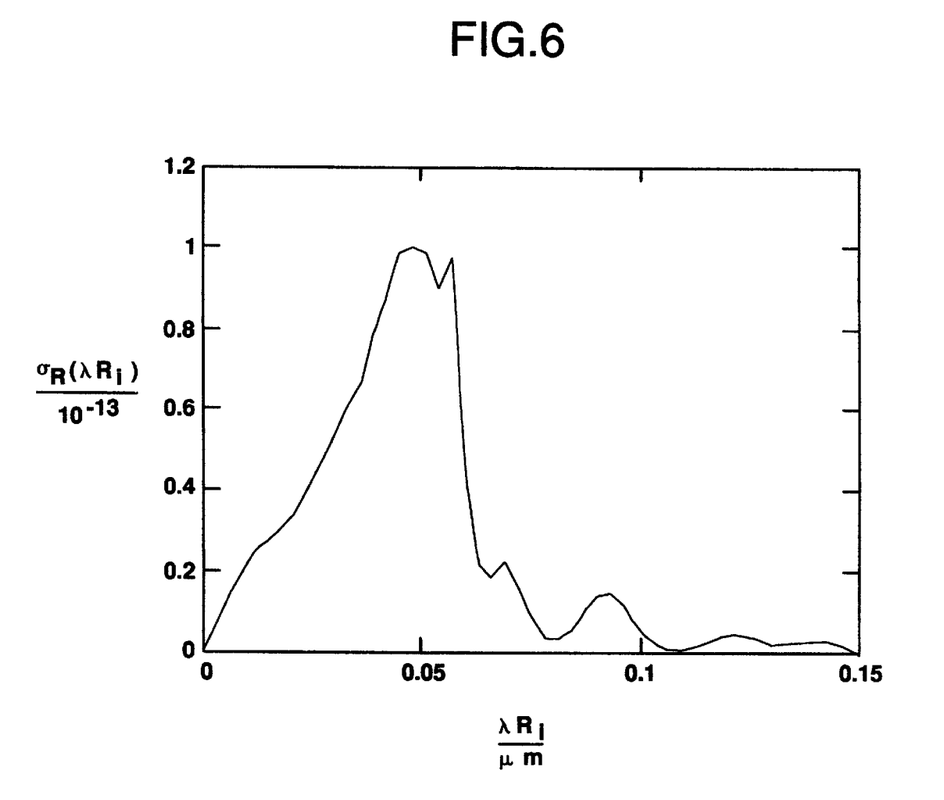
FIG. 6 is a curve depicting the Raman gain in an exemplary optical fiber cable core.

The SRS effect can best be understood by considering the laser pulse shapes and shapes of pulses transmitted through the fiber. The top trace of FIG. 6 depicts the shape of the pulse coming directly from a Nd:YAG laser without propagating through the fiber. The output pulse is approximately 100 $\mu$s long with a peak power of 500 watts with a brief burst of relaxation oscillations on the leading edge, chosen to simulate quasi-CW conditions in the fiber. The bottom three traces in FIG. 6 are the shapes of light pulses emitted from the fiber. The peak input power of 130 Watts is shown in the first trace, and the lower traces illustrate the temporal shapes of the 1.064 $\mu$m light, the 1st order Raman line and the 2nd order Raman line. Due to the highly nonlinear SRS process, small amplitude variations in the coupled light lead to large variations in the fundamental and Raman light components emitted from the optical fiber.

Figure 5:
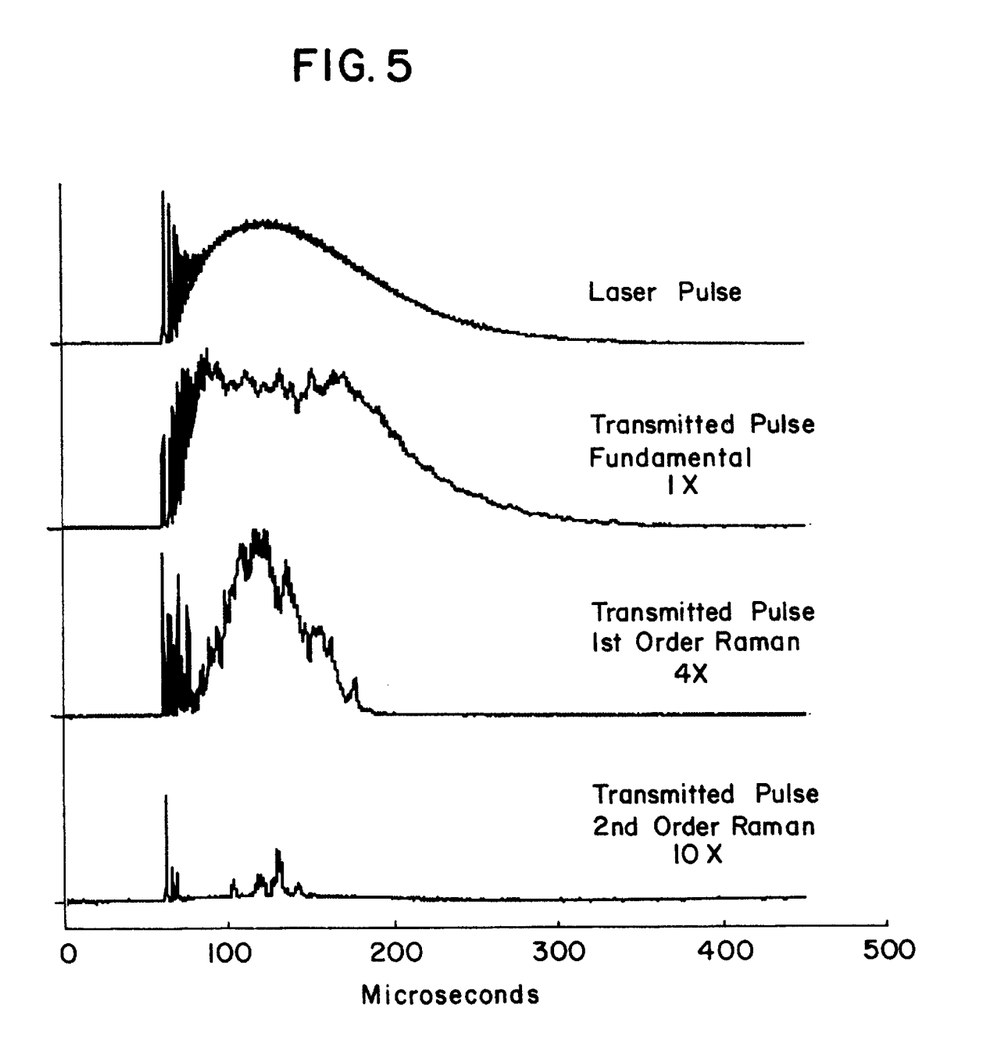
FIG. 5 presents a comparison of an input laser pulse, an amplified laser pulse, a first-order Raman pulse and a second order Raman pulse, looking top to bottom, with respect to identical time scales.

The fundamental-wavelength pulse with its flat top demonstrates the sharp threshold behavior described previously with respect to FIG. 5. Once the threshold is exceeded, additional coupled power is diverted from the fundamental wavelength into the Raman line. Adding the fundamental and 1st order Raman pulses together (note the waveform amplitude scaling) would result in a waveform similar to that of the original laser pulse in the top trace, consistent with the idea that most of the pulse energy is concentrated at the fundamental and 1st Raman wavelengths. The 2nd order Raman line at the 130 Watt peak power level is very small and flickers on and off from pulse to pulse. Its energy is insignificant compared to that at the other two wavelengths at this incident power level.

It should be pointed out that the SRS gain observed is for a high power signal propagating the entire length of the optical fiber. This is not the case for the proposed high power optical amplifier. The 1.06 $\mu$m signal is normally injected at a low level and it will gain power over the entire length of the optical amplifier. This gain of the 1.06 $\mu$m signal will effectively decrease the total Raman gain available because of the significantly decreased interaction length. Consequently, achieving 100 Watts CW from an optical amplifier will not be limited by SRS.

As discussed above, the nominal Raman shift is about 53 nm. In other instances, the gain coefficient for the Stimulated Raman Scattering in silica fibers peaks at approximately 40 nm from the original signal, as shown in FIG. 6. It will be appreciated that the Raman gain spectrum actually mirrors the LO phonon spectrum in the fiber core, which depends upon the composition of the glass used to form the core. It will also be appreciated that the first-order Raman line depicted in FIG. 3 is considerably broader than the fundamental line at 1.064 $\mu$m because of the broad Raman gain spectrum of silica glass shown in FIG. 6.

SRS occurs all along the optical fiber and it is characterized by a differential scattering cross section, which section is integrated over the solid angle of the numerical aperture of the fiber to determine the probability of a spontaneous Raman photon being captured by the fiber and creating the SRS wave. When SRS is present in the fiber or the potential for SRS is present, the power in the signal wave must be increased rapidly so that energy conversion occurs over as short of a fiber length as physically possible. As the high power propagates along the fiber, the Stokes wave begins to grow. If the desired signal power can be reached before the Stokes wave reaches threshold, then the high power fiber amplifier will operate efficiently. It will be appreciated that the Stokes wave threshold is the point at which the gain in the Stokes wave exceeds the distributed losses in the fiber. Consequently, by designing the fiber amplifier to have a distributed loss at the Stokes wavelength, it is possible to completely suppress the generation of the Stokes wave over relatively long fiber lengths.

Figure 7:
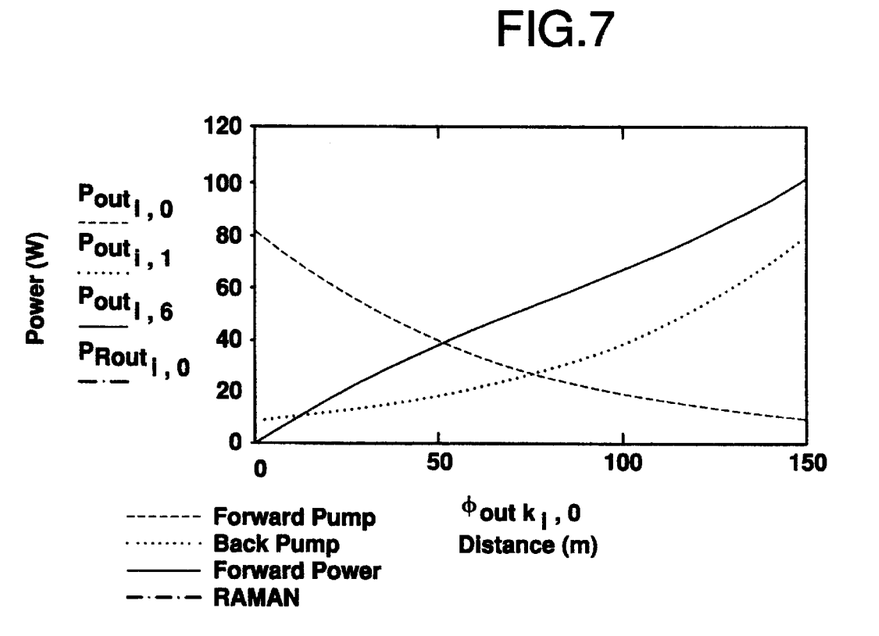
FIGS. 7 and 8 collectively illustrate operation in the gain band of the rare earth dopant used in the fiber amplifier core and Raman gain for relatively short and long optical fiber cables, respectively.
Figure 8:
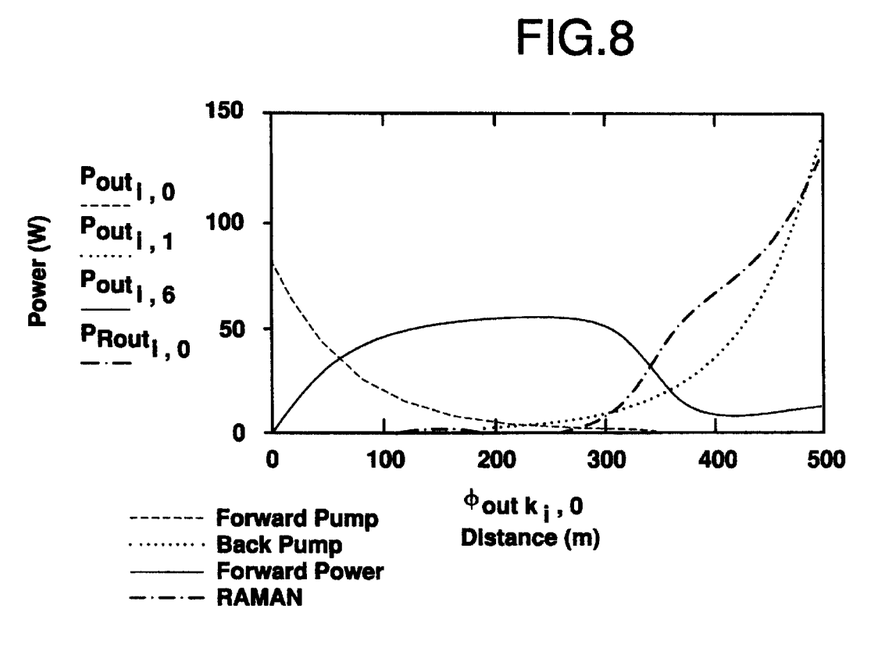

To see the effect of the build-up of Raman parasitics see FIGS. 7 and 8. In FIG. 7, a properly designed fiber amplifier pumped from both ends can amplify an input signal to the 100 watt level. In FIG. 8, a longer fiber, again pumped from both ends, allows the onset of parasitic Raman amplification gain, which depletes the signal power and converts it to the down-shifted Raman wavelength.

The master oscillator 100 signal is efficiently amplified by the array 200 of high power fiber optic amplifiers illustrated in FIG. 1 if no parasitic SRS occurs in the high power stages. This is assured by design of these amplifier stages. First, since the Raman gain is a function of the signal amplitude, the diameter of the fiber core can be increased within limits to reduce the intensity at a given signal power level. The limitation here is that the fiber should remain essentially single mode. Second, since the onset of the parasitic Raman signal is rather abrupt and depends on the level of down shifted Raman signal present, a Raman filter can be inserted between the tandem stages of each power amplifier line to impede the build up of the Raman signal. Thus in a prior art system, the Raman signal is a detrimental complication that must be controlled by design.

It will be appreciated that the MO-PPAA illustrated in FIG. 1 consists of a phased array of high power fiber optic amplifiers that amplify a signal within the gain band of the rare earth dopant used in the fiber amplifier core. This restricts the useful band of wavelengths to a few tens of nanometers for each of the limited number of rare earth dopants. Even though the output of such an array can be frequency doubled efficiently, the wavelength restriction mentioned immediately above applies equally to the possible harmonic wavelengths.

The possibility of operation of an efficient laser source at an arbitrary wavelength is an enormous advantage. What is needed is a narrow linewidth, single frequency-selectable solid state laser amplifier that is both compact and efficient. Preferably, such a laser amplifier would also be scaleable to a high average power. Most preferably, the postulated laser amplifier would have an output wavelength which is selectable over a range of hundreds of nanometers above the gain band of the rare earth dopant used in the fiber amplifier core. As a practical matter with respect to the laser "guidestar" application, what is needed is a laser amplifier producing a desired waveform having a 160 ms pulse burst of the short pulses described above at a 1 kHz burst rate.

SUMMARY OF THE INVENTION

Based on the above and foregoing, it can be appreciated that there presently exists a need in the art for a laser amplifier system which overcomes the above-described deficiencies. The present invention was motivated by a desire to overcome the drawbacks and shortcomings of the presently available technology, and thereby fulfill this need in the art.

A first object according to the present invention is to provide a narrow linewidth, single frequency-selectable solid state laser amplifier that is both compact and efficient. According to one aspect of the present invention, the laser amplifier advantageously can be scaleable to a high average output power.

Another object according to the present invention is to provide a laser amplifier whose output wavelength is freely selectable over a range of hundreds of nanometers above the gain band of the rare earth dopant used in the fiber amplifier core.

Still another object according to the present invention is to provide a laser amplifier producing a waveform having a 160 ms pulse burst above at a 1 kHz burst rate for generating an artificial laser "guidestar". The present invention advantageously can generate such a waveform readily. Moreover, the basic architecture disclosed can be adapted to produce high power at other arbitrary wavelengths for specific applications. Advantageously, the present invention also provides a method to scale-up this approach to produce tens or hundreds of watts of output laser power, as needed. Thus, the present invention encompasses a method and corresponding apparatus for generating high laser power at these very precise wavelengths with high efficiency and near diffraction limited output beam quality.

A still further object according to the present invention is to provide a phased array Raman laser amplifier which can be constructed from a few discrete modules so as to permit at least the power amplifier stage of the phased array Raman laser amplifier to be scaled up to any desired size. Thus, according to one aspect of the present invention, the modularity of the phased array Raman laser amplifier facilitates production of a high power output laser beam at the Raman wavelength.

Yet another object according to the present invention is to provide a phased array Raman laser amplifier having a high efficiency.

Another object according to the present invention is to provide a phased array Raman laser amplifier exhibiting wavelength diversity.

A further object according to the present invention is to provide a phased array Raman laser amplifier producing an output laser beam of high beam quality.

Although various applications will stress different aspects of the basic invention, the benefits of the invention are the generation of a high power laser beam at an arbitrary wavelength with high efficiency while maintaining overall excellent beam quality. The same system architecture will serve to produce an expansive range of output powers over a wide range of wavelengths with only minor architectural variations.

These and other objects, features and advantages according to the present invention are provided by a phased array Raman laser amplifier including a beam generator for generating a fundamental laser beam and a Raman seed frequency laser beam, and a fiber optic laser amplifier for forming a diffraction limited output laser beam at the Raman seed frequency by amplifying the fundamental laser beam to a power level corresponding to the Stimulated Raman Scattering (SRS) threshold to thereby pump the SRS process and provide Raman gain to the Raman seed frequency laser beam. According to one aspect of the present invention, the fiber optic laser amplifier includes a beam splitter receiving the fundamental laser beam and the Raman seed frequency laser beam and generating N secondary fundamental and N Raman seed frequency laser beams, N parallel rare earth doped optical fiber sections, each of the optical fiber sections amplifying a respective one of the N secondary fundamental laser beams to thereby produce N tertiary laser beams at the power level corresponding to the Stimulated Raman Scattering (SRS) threshold to thereby pump the SRS process and provide Raman gain to the N Raman seed frequency laser beams to thereby produce N amplified Raman seed frequency laser beams, and an optical combiner for receiving at least the N Raman seed frequency laser beams and for generating the diffraction limited output laser beam at the Raman seed frequency. Preferably, N is an integer greater than or equal to 2. In an exemplary case, each of the optical fiber sections includes a Yb:Er core. In another exemplary case, each of the optical fiber sections includes a Nd doped core. Advantageously, the N optical fiber sections are connected to the combiner by a fiber optic bundle.

These and other objects, features and advantages according to the present invention are provided by a phased array Raman laser amplifier including:

- a first device for generating a fundamental laser beam;
- a second device for generating a Raman seed frequency laser beam;
- a third element for combining the fundamental laser beam and the Raman seed frequency laser beams;
- a fourth element for generating N fundamental laser beams and for generating N Raman seed frequency laser beams responsive to the combined the fundamental laser beam and the Raman seed frequency laser beams;
- a fifth element for amplifying the power level of each of the N fundamental laser beams to the Stimulated Raman Scattering (SRS) threshold associated with the fifth element to thereby pump the SRS process so as to provide Raman gain for each of the N Raman seed frequency laser beams to thereby produced N amplified Raman seed frequency laser beams; and
- a sixth element for combining the N amplified Raman seed frequency laser beams to thereby produce a diffraction limited output laser beam.

These and other objects, features and advantages according to the present invention are provided by a method for operating a phased array Raman laser amplifier having a beam generator for generating a fundamental laser beam and a Raman seed frequency laser beam and a fiber optic laser amplifier for forming a diffraction limited output laser beam at the Raman seed frequency by amplifying the fundamental and Raman seed frequency laser beams by Stimulated Raman Scattering (SRS). Preferably, the method includes steps for:

(a) generating a fundamental laser beam;
(b) generating a Raman seed frequency laser beam;
(c) generating N fundamental laser beams responsive to the fundamental laser beam;
(d) generating N Raman seed frequency laser beams responsive to the Raman seed frequency laser beam;
(e) amplifying the power level of each of the N fundamental laser beams to the Stimulated Raman Scattering (SRS) threshold associated with the fiber optic laser amplifier to thereby pump the SRS process so as to provide Raman gain for each of the N Raman seed frequency laser beams; and
(f) combining the N amplified Raman seed frequency laser beams to thereby produce a diffraction limited output laser beam.

According to one aspect of the inventive method, step (f) includes the sub-steps of:

(f)(i) doubling the frequency of each of the N amplified Raman seed frequency laser beams so as to produce N frequency doubled laser beams; and
(f)(ii) combining the N frequency doubled laser beams to thereby produce the diffraction limited output laser beam.

These and other objects, features and advantages of the invention are disclosed in or will be apparent from the following description of preferred embodiments.

BRIEF DESCRIPTION OF THE DRAWINGS

These and various other features and aspects of the present invention will be readily understood with reference to the following detailed description taken in conjunction with the accompanying drawings, in which like or similar numbers are used throughout, and in which.

DETAILED DESCRIPTION OF THE PREFERRED EMBODIMENTS

Figure 9:
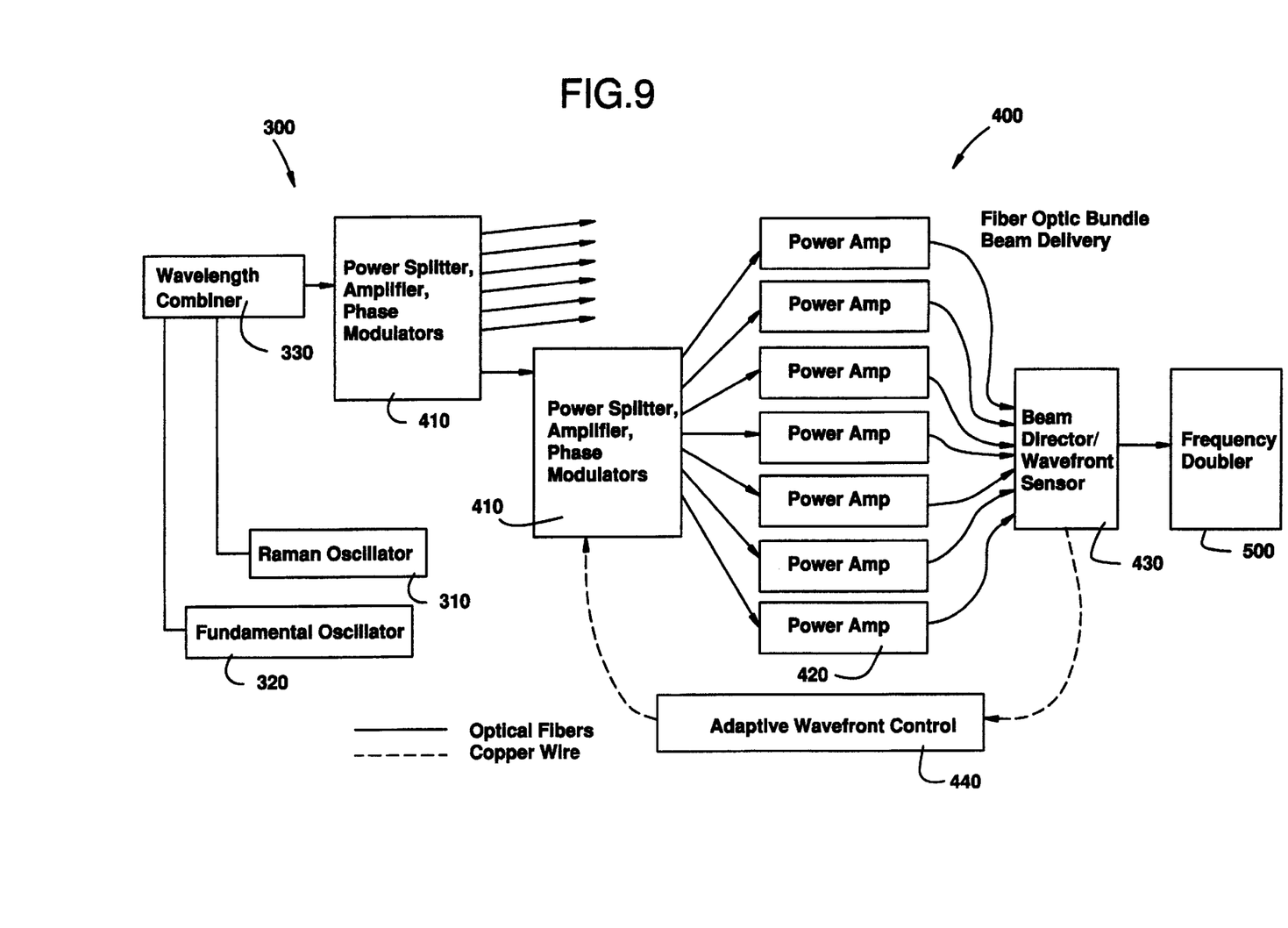
FIG. 9 is a high level block diagram of a phased array Raman laser amplifier according to the percent invention.

A preferred embodiment according to the present invention will now be described with reference to FIG. 9, wherein the phased array Raman laser amplifier includes a laser source generator 300, a Raman amplifier array 400 and a frequency doubler 500. As will appreciated from the discussion which follows, although the phased array Raman laser amplifier according to the present invention appears to be similar to that employed in a proposed phased array laser amplifier illustrated in FIG. 1, at first glance, the operation of the phased array laser amplifiers illustrated in FIGS. 1 and 9 are markedly different. In the proposed system of FIG. 1, Stimulated Raman Scattering (SRS) is considered an undesirable parasitic effect that must be controlled to avoid loss of output signal. In contrast, the present invention advantageously employs SRS to effect a conversion of the fundamental wavelength of the fiber amplifier array, i.e., of the rare earth dopant used, to the desired operating wavelength by one or more Raman scattering steps.

While fiber optic Raman lasers and amplifiers are not new, their use in a high power coherent phased array has not heretofore been suggested. Moreover, inasmuch as a Raman amplifier according to the present invention is novel, the combination of the Raman amplifier array with a known frequency doubler, either within the final power amplifier stage or downstream of the final power amplifier stage, has never before been suggested or proposed.

Advantageously, the laser source generator 300 includes at least one Raman generator 310 for generating at least one laser beam at the Raman seed frequency, a fundamental oscillator 320 for generating a fundamental laser beam having a frequency corresponding to the gain frequency of the rare earth doped optical fibers employed in the array 400, and a wavelength combiner 330, for combining the Raman seed frequency laser beam and the fundamental laser beam for application to the array 400. It should be mentioned that the wavelength combiner 330 advantageously can be either an active or passive device; most preferably, the wavelength combiner 330 is a member of the class of devices generally denoted a wavelength division multiplexer (WDM).

Preferably, the Raman generator 310 generates at least one Raman seed frequency laser beam, i.e., a laser beam having an output wavelength approximately equal to the desired output laser beam. It should be mentioned that laser beams at intermediate Raman shifted wavelengths advantageously can be provided by the Raman generator 310. For the exemplary "guidestar" application, it will be appreciated that the desired output laser beam has a 1179 nm wavelength and that an exemplary silica glass optical fiber produces a Raman down shift, often referred to as a Stokes shift, of 53 nm, nominally. Given a fundamental laser having a nominal 1064 nm wavelength, it will be appreciated that both a first order Raman laser beam at 1117 nm and a second order Raman laser beam at 1179 nm would both advantageously be generated by Raman generator 310 and provided to array 400. As a practical matter, the second order Raman laser beam, i.e., the Raman seed frequency laser beam, would be locked to the wavelength of the desired output laser beam, i.e., 1179 nm. Advantageously, since the output of the fundamental oscillator 320 is selectable over a range measured in tens of nanometers, a 1073 nm fundamental laser beam can be coupled to the array 400 via the wavelength combiner 330 such that the difference between the wavelengths of the fundamental laser beam and the desired output laser beam is 106 nm±10 nm, i.e., two Raman shifts for the exemplary optical fiber.

Still referring to FIG. 9, it will be appreciated that the power splitter, amplifier and phase modulator elements 410 may be arranged in various configurations other than the exemplary arrangement illustrated in that Figure. The illustrated fiber optic power amplifier 400 of FIG. 9 includes a first stage composed of a first beam splitter element 410, for splitting a received laser beam into a number N of secondary laser beams. Each of the secondary laser beams is provided to a second beam splitter element 410, which produces a number M of tertiary laser beams from a respective one of the secondary laser beams. Each of the tertiary laser beams is amplified by a respective fiber power amplifier generally denoted 420. It should be mentioned that although two separate stages of beam splitter elements 410 and one amplifier stage 420 are depicted in FIG. 9, the fiber optic power amplifier 400 according to the present invention beneficially can have more or less amplification stages. For example, when the first and second beam splitter elements 420 include an optical amplifier 16 pumped by a pump source 18, a beam splitter 24 and, optionally, a number N×M phase modulators, respectively, a total of three amplification devices are included in the power amplifier 400. See FIG. 2a.

Preferably, the fundamental laser beam at the fundamental wavelength is injected into the input port of the array 400 as shown, and the fundamental laser beam is amplified in each fiber beam line to a level sufficient to pump the SRS process in the power amplifier stage 420, which in turn provides Raman gain for the Raman signal to be amplified. As mentioned previously, the desired laser beam to be amplified at the Raman wavelength is simultaneously injected into the phased array input port through the wavelength combiner 330 as shown.

Figure 10:
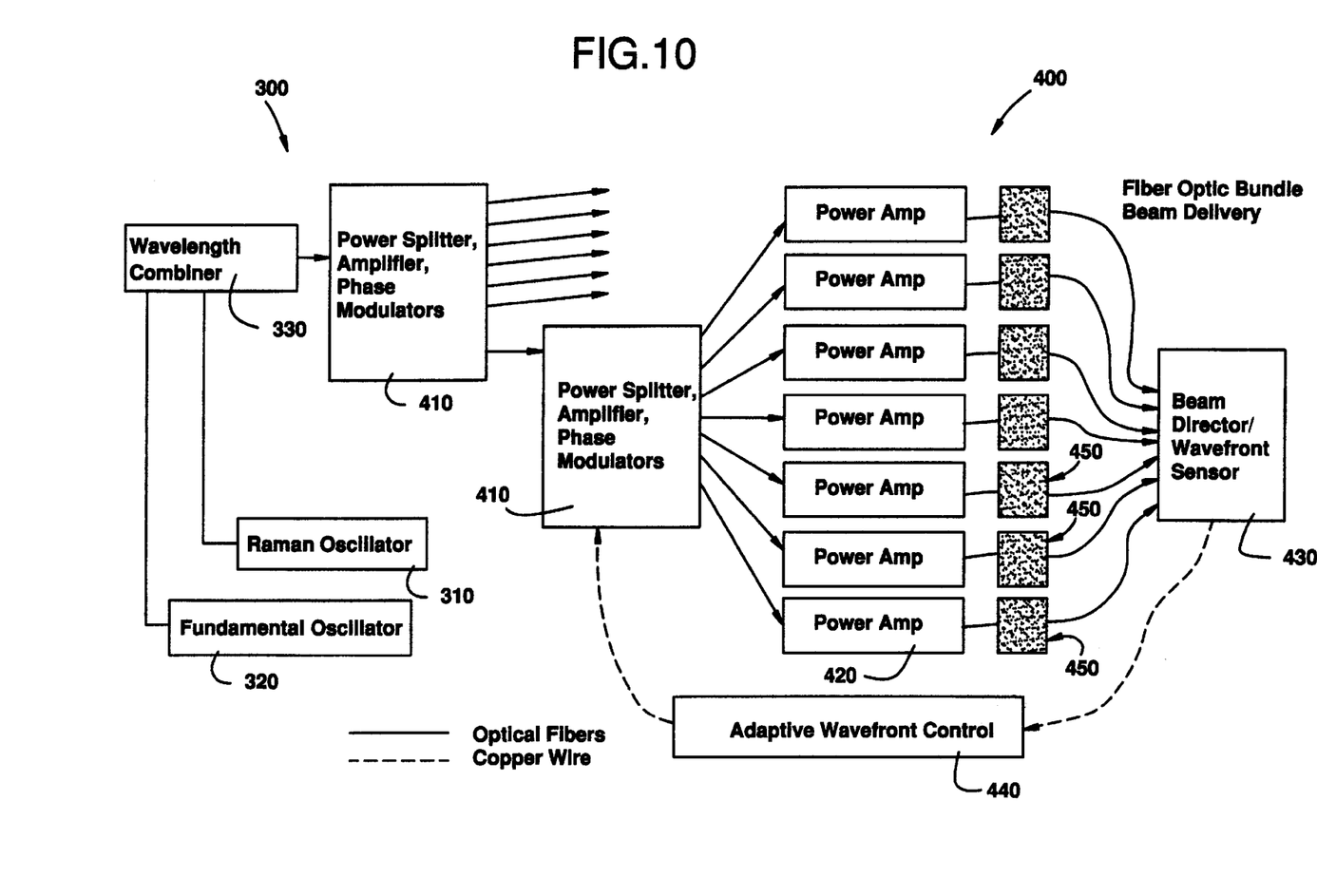
FIG. 10 is a high level block diagram of an alternative phased array Raman laser amplifier according to the present invention.

Advantageously, the desired output laser beam at the Raman wavelength is sensed by beam director/wavefront sensor 430 so that the phase of each beam line beneficially can be adjusted electronically using the adaptive wavefront controller 440 to form a diffraction limited beam. It will be appreciated that the same control system and beam forming algorithms used to form a fundamental wavelength beam in FIG. 1 can be used to form the Raman wavelength beam in the phased array Raman laser amplifier illustrated in FIG. 9. Advantageously, the desired output laser beam can be frequency doubled either by a single nonlinear crystal 500 depicted in FIG. 9, or by an array of nonlinear crystals, generally denoted 450, located immediately downstream of the power amplifiers 420. It will be appreciated that the configuration of FIG. 10 is advantageous for very high average power applications.

It should be mentioned that various filters such as a notch filter advantageously can be used to ensure that the desired output laser beam is effectively separated from the lower power fundamental and first order Raman laser beams produced by the power amplifiers 420. Since the frequency doubler 500 is itself a nonlinear device adapted to the desired output laser beam, filtering of the desired output laser beam advantageously can be omitted.

As discussed above, the desired wavelength to be amplified can be generated with high precision but low efficiency at a low power. For applications that involve atomic resonance, the frequency can be actively locked using an appropriate absorption cell. Preferably, active locking is performed in the Raman oscillator 310 such the Raman laser beam wavelength is an integer multiple of the wavelength of the desired output laser beam. This is true also if the signal is at a harmonic wavelength.

Moreover, as previously discussed, more than one Raman (Stokes) down shift may be required to achieve the desired wavelength; in this case, multiple Raman wavelengths advantageously can be injected into the phased array 400. Thus, the first Stokes wavelength depletes the fundamental wavelength in the fiber, the second Stokes wavelength depletes the first Stokes wavelength as it builds up in the fiber, and so on to the desired wavelength to be amplified. It should also be mentioned that once the desired Stokes wavelength builds up in the fibers of the power amplifiers 420 precautions must be taken to prevent further Raman shifts, as noted previously, by design or filtering.

The two examples cited, an artificial laser "guidestar" and isotope separation are very important for both commercial and military applications. Moreover, the present invention is advantageous in a variety of other applications. For example, the wavelength diversity of the preferred embodiments according to the present invention are easily adapted to remote sensing of some significant chemical species using Differential Absorption Lidar (DIAL) systems. In addition to isotope separation, the present invention would also have applications in photochemistry. An important medical application involves the ability of the present invention to produce precise wavelengths for exciting specific dyes used in photodynamic therapy, for which specifically "tuned" dyes are effective against specific tumors. Furthermore, there are several laser countermeasure applications wherein the ability to generate arbitrary wavelengths advantageously can be used to defeat counter-countermeasures such as filters. The present invention can produce high power red, blue, and green wavelengths appropriate for ultra-bright high resolution laser projectors. Advantageously, the tunable output of the laser beam generated by the present invention could be used to pump a variety of solid state lasers with absorption bands in the near infrared. The present invention could also be used in pumping high power optical parametric oscillators (OPOs) for mid-infrared countermeasures applications.

While the present invention was discussed with respect to a single optical fiber type, the present invention is not limited to a single optical fiber type or even an amplifier array utilizing optical fibers. The present invention works for any rare earth dopant; Raman shifts from starting wavelengths such as 2.05 $\mu$m or longer would enable high power mid-infrared sources. Advantageously, the rare earth doped optical fiber can be fabricated using Nd, Yb, Yb:Er, Er, Pr, and Ho, or combinations thereof, as the dopant. Moreover, it will be appreciated that the present invention is not limited to arrays of rare earth doped optical fibers; semiconductor arrays advantageously can be used where minimal output power and maximum bandwidth are the essential design constraints.

It will be appreciated that a single beam line Raman shifted amplifier, which is prior art, is both similar to and fundamentally different from a phased array of such devices. For example while both could be used to produce a precise frequency, for example, as required to excite sodium atoms in the "guidestar" application, the capability to scale-up the output power to the level likely to be needed, or to any arbitrary level, would be lacking in the single beam line Raman shifted amplifier since there are real limitations on the capability of single mode fibers to transmit power. An array of fiber amplifiers allows scaling-up by combining additional fiber amplifiers coherently. Moreover, the active beam sensing and control system provided by elements 430 and 440 of the power amplifier array 400 achieves a diffraction limited output for an arbitrary number of fibers, i.e., any number of power amplifiers 420.

Likewise, were it possible to generate an arbitrary power level from a single, prior art Raman fiber amplifier, it would not be possible to frequency double an arbitrarily high power using physically realizable nonlinear crystals. Hence, the possibility of using an array of nonlinear crystals in a phased coherent array frequency doubler allows generation of a diffraction limited second harmonic beam at an arbitrarily high power.

As discussed above, the Raman gain is broadly centered about a wavelength about 53 nm longer than the incoming laser beam's wavelength, depending upon the composition of the fiber core but not the laser beam's wavelength. However, as illustrated in FIGS. 3 and 6, the Raman gain is concentrated in a wavelength region and not in a single wavelength; the Raman laser gain region allows selection of the desired output laser wavelength from any frequency within the Raman gain region. In the exemplary case under discussion, the output Raman laser beam advantageously can be built up from spontaneous Raman scattering, i.e., signal photons in elastically scattered from phonons with a loss of energy and subsequent increase in wavelength. It will be appreciated that it is the stimulated Raman scattering process, i.e., amplification of photons present at the downshifted wavelength, that makes SRS a problematic parasitic process in the array 200 of FIG. 1. However, it is SRS that enables Raman amplifier designs to cover wavelengths that can not be amplified by conventional rare earth doped amplifiers.

It should be mentioned briefly that a Raman amplifier is not as efficient as the amplifier that pumps it, since energy is lost to phonons and a small amount of the pumping signal is not converted. However, the power loss penalty can be considered a minor cost when compared to the overall wavelength flexibility provided by the phased array Raman laser amplifier according to the present invention. Of course, the high power first Raman signal can induce a second Raman parasitic and so on, as specifically depicted in FIG. 3.

It should also be mentioned that various modifications to the present invention can be made without departing from the present invention. In particular, since the elements in the power amplifier array 400 are nonlinear elements, various design parameters advantageously can be adjusted to tune the phased array Raman laser amplifier to the intended application. For example, it will be appreciated that the onset of SRS advantageously can be controlled by controlling the length of the optical fiber in power amplifier 420 or the cross section of the optical fiber of power amplifier 420, or both. Moreover, as discussed above, variations in the dopant and the material making up the rare earth doped optical fiber advantageously can be used to control the onset of SRS. It will be appreciated that the required gain for the fundamental laser beam in the elements 410 can be determined once the characteristics of the power amplifiers 420 are selected.

In summary, the preferred embodiment according to the present invention is a phased array Raman laser amplifier composed of all solid state elements. The present invention has many desirable features, such as modularity, high power, high efficiency, wavelength diversity, making the phased array Raman laser amplifier desirable over other laser systems having similar operating frequencies.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. A phased array Raman laser amplifier comprising:
   a beam generator for generating a fundamental laser beam and a Raman seed frequency laser beam; and
   a laser amplifier array for forming a diffraction limited output laser beam at the Raman seed frequency by amplifying said fundamental laser beam to a power level corresponding to a Stimulated Raman Scattering (SRS) threshold to thereby pump the SRS process and provide Raman gain to the Raman seed frequency laser beam.

2. The phased array Raman laser amplifier as recited in claim 1, wherein said beam generator comprises:
   a fundamental oscillator for producing said fundamental laser beam;
   a Raman oscillator for producing said Raman seed frequency laser beam; and
   a wavelength combiner for combining and applying said fundamental laser beam and said Raman seed frequency laser beam to said laser amplifier array.

3. The phased array Raman laser amplifier as recited in claim 2, wherein said Raman oscillator is a locked frequency Raman oscillator.

4. The phased array Raman laser amplifier as recited in claim 1, further comprising a frequency doubler for doubling the frequency of the diffraction limited output laser beam so as to produce a frequency doubled diffraction limited output laser beam.

5. The phased array Raman laser amplifier as recited in claim 4, wherein said laser amplifier array comprises:

a beam splitter receiving said fundamental laser beam and said Raman seed frequency laser beam and generating N secondary fundamental and N Raman seed frequency laser beams;

N parallel rare earth doped optical fiber sections, each of said optical fiber sections amplifying a respective one of said N secondary fundamental laser beams to thereby produce N tertiary laser beams at the power level corresponding to a Stimulated Raman Scattering (SRS) threshold to thereby pump the SRS process and provide Raman gain to the N Raman seed frequency laser beams to thereby produce N amplified Raman seed frequency laser beams; and an optical combiner for receiving at least said N Raman seed frequency laser beams and for generating said diffraction limited output laser beam at the Raman seed frequency;

wherein N is an integer greater than or equal to 2.

6. The phased array Raman laser amplifier as recited in claim 1, wherein said laser amplifier array comprises:

a beam splitter receiving said fundamental laser beam and said Raman seed frequency laser beam and generating N secondary fundamental and N Raman seed frequency laser beams; and N parallel rare earth doped optical fiber sections, each of said optical fiber sections amplifying a respective one of said N secondary fundamental laser beams to thereby produce N tertiary laser beams at the power level corresponding to a Stimulated Raman Scattering (SRS) threshold to thereby pump the SRS process and provide Raman gain to the N Raman seed frequency laser beams to thereby produce N amplified Raman seed frequency laser beams; and an optical combiner for receiving at least said N Raman seed frequency laser beams and for generating said diffraction limited output laser beam at the Raman seed frequency;

wherein N is an integer greater than or equal to 2.

7. The phased array Raman laser amplifier as recited in claim 6, wherein each of said optical fiber sections comprises a doped single mode optical fiber core, and wherein a dopant is selected from a group consisting of Nd, Yb, Yb:Er, Er, Pr, Ho, and a semiconductor material.

8. The phased array Raman laser amplifier as recited in claim 6, wherein said N optical fiber sections are connected to said combiner by a fiber optic bundle.

9. A phased array Raman laser amplifier comprising:

first means for generating a fundamental laser beam;

second means for generating a Raman seed frequency laser beam;

third means for combining said fundamental laser beam and said Raman seed frequency laser beams;

fourth means for generating N fundamental laser beams and for generating N Raman seed frequency laser beams responsive to the combined fundamental laser beam and Raman seed frequency laser beams;

fifth means for amplifying the power level of each of said N fundamental laser beams to a Stimulated Raman Scattering (SRS) threshold associated with said fifth means to thereby pump the SRS process so as to provide Raman gain for each of said N Raman seed frequency laser beams to thereby produced N amplified Raman seed frequency laser beams; and sixth means for combining said N amplified Raman seed frequency laser beams to thereby produce a diffraction limited output laser beam.

10. The phased array Raman laser amplifier as recited in claim 9, wherein said sixth means comprises:

seventh means for doubling the frequency of each of said N amplified Raman seed frequency laser beams so as to produce N frequency doubled laser beams; and eighth means for combining said N frequency doubled laser beams to thereby produce the diffraction limited output laser beam.

11. The Phased array Raman laser amplifier as recited in claim 9, wherein:

said second means comprises means for generating first and second Raman seed frequency laser beams each having a different frequency;

said third means comprises means for combining said fundamental laser beam and said first and second Raman seed frequency laser beams;

said fourth means comprises means for generating N fundamental laser beams and for generating N first and second Raman seed frequency laser beams responsive to the combined fundamental laser beam and first and second Raman seed frequency laser beams; and said fifth means comprises means for amplifying the power level of each of said N fundamental laser beams to the Stimulated Raman Scattering (SRS) threshold associated with said fifth means to thereby pump the SRS process so as to provide Raman gain for each of said N first and second Raman seed frequency laser beams to thereby produce N amplified Raman seed frequency laser beams at the second Raman seed frequency.

12. A method for operating a phased array Raman laser amplifier having a beam generator for generating a fundamental laser beam and a Raman seed frequency laser beam and a fiber optic laser amplifier for forming a diffraction limited output laser beam at the Raman seed frequency by amplifying the fundamental and Raman seed frequency laser beams by Stimulated Raman Scattering (SRS), the method comprising the steps of:

(a) generating a fundamental laser beam;

(b) generating a Raman seed frequency laser beam;

(c) generating N fundamental laser beams responsive to said fundamental laser beam;

(d) generating N Raman seed frequency laser beams responsive to said Raman seed frequency laser beam;

(e) amplifying the power level of each of said N fundamental laser beams to a Stimulated Raman Scattering (SRS) threshold associated with the fiber optic laser amplifier to thereby pump the SRS process so as to provide Raman gain for each of said N Raman seed frequency laser beams to thereby produced N amplified Raman seed frequency laser beams; and (f) combining said N amplified Raman seed frequency laser beams to thereby produce the diffraction limited output laser beam.

13. The method for operating the Phased array Raman laser amplifier as recited in claim 12, wherein said step (f) comprises the steps of:

(f)(i) doubling the frequency of each of said N amplified Raman seed frequency laser beams so as to produce N frequency doubled laser beams; and (f)(ii) combining said N frequency doubled doubled laser beams to thereby produce a diffraction limited output laser beam.

14. A method for generating a precise output wavelength in a laser amplifier array comprising the steps of:

applying a frequency-locked Raman seed frequency laser beam and a fundamental laser beam to the laser amplifier array; and generating an output laser beam using a Stimulated Raman Scattering (SRS) process whereby the majority of the power of said output laser beam is at the frequency-locked Raman seed frequency.

15. The method as recited in claim 14, wherein the frequency-locked Raman seed frequency is absolutely controlled to an atomic transition required for producing an artificial laser guidestar.

16. The method as recited in claim 14, wherein the frequency-locked Raman seed frequency is absolutely controlled so as to permit separation of a desired isotope from a material including several isotopes of an element.

* * * * *